(12) United States Patent
Sirohey et al.

(10) Patent No.: US 7,868,900 B2
(45) Date of Patent: Jan. 11, 2011

(54) METHODS FOR SUPPRESSION OF ITEMS AND AREAS OF INTEREST DURING VISUALIZATION

(75) Inventors: Saad Ahmed Sirohey, Pewaukee, WI (US); Gopal B. Avinash, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 1287 days.

(21) Appl. No.: 10/844,073

(22) Filed: May 12, 2004

(65) Prior Publication Data

US 2005/0256399 A1 Nov. 17, 2005

(51) Int. Cl.
*G09G 5/02* (2006.01)
*G06K 9/40* (2006.01)
*G06K 9/00* (2006.01)
*G06K 9/38* (2006.01)
*G06K 9/42* (2006.01)

(52) U.S. Cl. .................. 345/592; 382/275; 382/128; 382/172; 382/256; 382/260

(58) Field of Classification Search .............. 345/592; 382/275, 128–132, 172, 256–257, 260, 270
See application file for complete search history.

(56) References Cited

U.S. PATENT DOCUMENTS

| | | | |
|---|---|---|---|
| 6,343,936 B1 | 2/2002 | Kaufman et al. | |
| 6,514,082 B2 | 2/2003 | Kaufman et al. | |
| 6,658,080 B1 | 12/2003 | Poole et al. | |
| 6,791,573 B2* | 9/2004 | Hamburg | 345/619 |
| 2005/0065424 A1* | 3/2005 | Shah et al. | 600/407 |
| 2005/0190955 A1* | 9/2005 | Brown | 382/128 |

OTHER PUBLICATIONS

Zack, G.W. et al., Automatic Measurement of Sister Chromatid Exchange Frequency, The Journal of Histochemistry and Cytochemistry, vol. 25, No. 7 (1977) pp. 741-753.
Bartroli, A.V., Wegenkittl, R., Konig, A., and Groller, E., Nonlinear Virtual Colon Unfolding, IEEE Proceedings: Visualization, 2001, pp. 411-418.

* cited by examiner

*Primary Examiner*—Xiao M Wu
*Assistant Examiner*—Tize Ma
(74) *Attorney, Agent, or Firm*—Armstrong Teasdale LLP

(57) ABSTRACT

A method for generating an image includes accessing data of a scan of an object, using at least one characteristic of the accessed data to delineate at least one item of interest in the data and generating a 3D visualization image wherein transparency levels for at least some pixels not representing the item of interest are set according to a first set of rules, and transparency levels for at least some pixels representing an interior portion of the item of interest are set according to a second set of rules different than the first set of rules, and at least some pixels representative of a transition area are set according to a third set of rules different than the first and second sets of rules.

26 Claims, 8 Drawing Sheets

METHODS FOR SUPPRESSION OF ITEMS AND AREAS OF INTEREST DURING VISUALIZATION

BACKGROUND OF THE INVENTION

Colon cancer is the third leading cause of cancer related mortality in the United States. Studies indicate that approximately 57,000 people died due to colon cancer in 2003 in the United States alone. With the removal of abnormal growths or polyps, which are a pre-cancerous stage of colon cancer, a patient has a 90% chance of survival 5 years after the removal.

The accepted standard for screening colon cancer is colonoscopy. However, colonoscopy is an invasive test, and hence has a low acceptance probability among patients. Computed tomography (CT) colonography is a test for screening for colon cancer using CT scanning. CT colonography involves minimal invasion. However, the sensitivity of CT colonography is lower than that of colonoscopy.

There exist advanced methods to increase the sensitivity of colonography. One method involves a fly-through three-dimensional visualization of a segmented colon using volume rendering techniques. Another method involves rendering and studying a virtually dissected colon. This method is described in a paper titled "Virtual Colon Unfolding" by Bartroli et al., published as a part of the IEEE proceedings on Visualization in 2001. Both these methods rely on mapping intensity values obtained from a CT scanner to a volume rendered three-dimensional view.

The presence of fecal matter in a colon can obstruct the visualization of anatomical details within such three dimensional views. Fecal matter acts as a source of false positives as it visually resembles abnormal growths within the colon. Hence, the removal of fecal matter from a CT image of a colon leads to an increase in the sensitivity of CT colonography.

BRIEF DESCRIPTION OF THE INVENTION

In one aspect, a method for generating an image is provided. The method includes accessing data of a scan of an object, using at least one characteristic of the accessed data to delineate at least one item of interest in the data and generating a 3D visualization image wherein transparency levels for at least some pixels not representing the item of interest are set according to a first set of rules, and transparency levels for at least some pixels representing an interior portion of the item of interest are set according to a second set of rules different than the first set of rules, and at least some pixels representative of a transition area are set according to a third set of rules different than the first and second sets of rules.

In another aspect, a method for generating an image includes accessing data of a scan of an object, generating a 3D visualization image of the object, performing a segmentation process on the generated 3D visualization image to generate a segmentation mask of an area of interest, and generating a 2D reformatted view using the accessed data and the generated segmentation mask such that the area of interest is at least partially removed from the 2D view.

In yet another aspect, a method for generating an image includes accessing data of a scan of an object, generating a 3D visualization image of the object, performing a segmentation process on the generated 3D visualization image to segment an area of interest, and varying transparency values of the 3D visualization image based upon the segmentation.

In yet another aspect, a method for generating an image is provided wherein the method includes accessing data of a scan of an object, generating a 3D visualization image of the object, receiving an indication of an area of interest, performing a segmentation process on the generated 3D visualization image to segment the area of interest, and varying transparency values of the 3D visualization image based upon the segmentation.

DETAILED DESCRIPTION OF THE INVENTION

The present disclosure relates to methods for suppressing virtual objects during visualization. Hereinafter, these methods are explained with the help of a colonography application, wherein the appearance of fecal matter is suppressed. However, it will be apparent to those skilled in the art that the method may be utilized to suppress the appearance of any object in a visualization or scan. For example, the method can be used to suppress the appearance of bones in a visualization of blood vessels.

Figure 1:
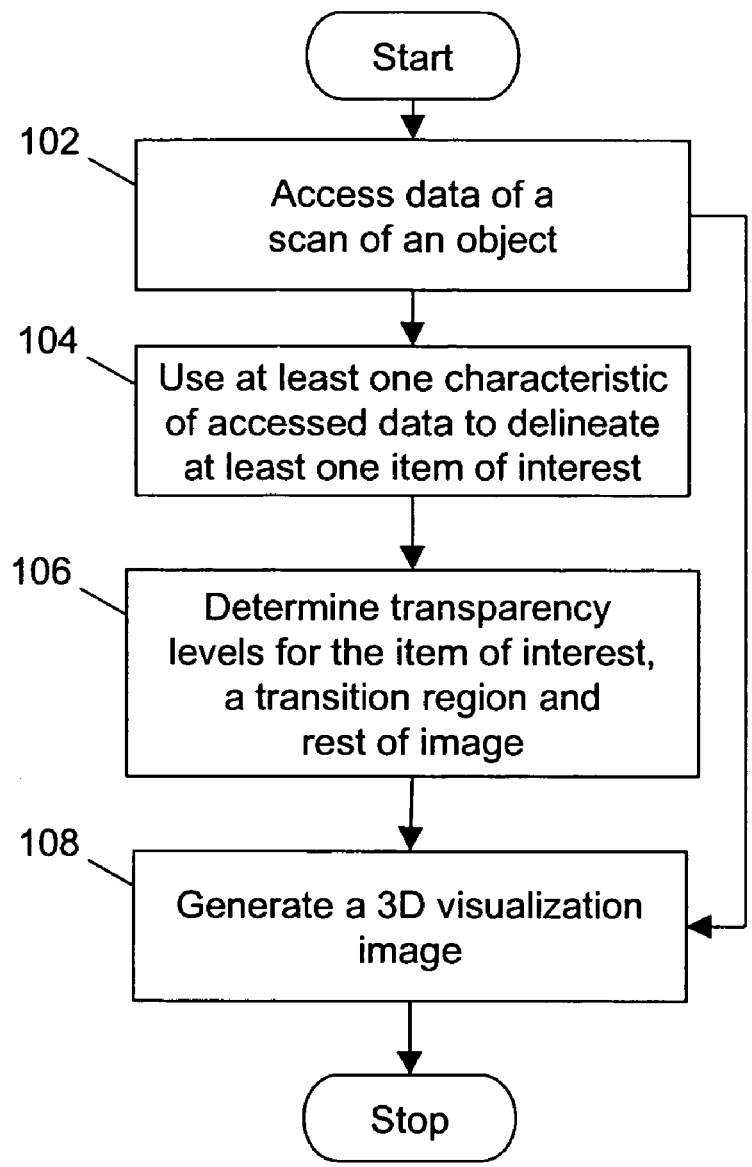
FIG. 1 is a flowchart illustrating the steps for suppressing at least one item of interest during visualization in accordance with one embodiment of the present invention.

FIG. 1 is a flowchart illustrating the steps for suppressing at least one item of interest during visualization in accordance with one embodiment of the present invention. At step 102, data of a scan of an object is accessed. This data is obtained, for example, from a computed tomography scanner that scans the object. At step 104, characteristics of the data accessed at step 102 are used to delineate at least one item of interest. Levels of transparency of various regions or sets of voxels within the 3D visualization image are determined at step 106. Voxels are volume elements of the 3D (three dimensional) visualization image. At step 108, a 3D visualization image is generated based on the data accessed at step 102 and the transparency levels determined at step 106. The 3D visualization image can also be generated, as shown at step 108, using only the data accessed at step 102.

Figure 2:
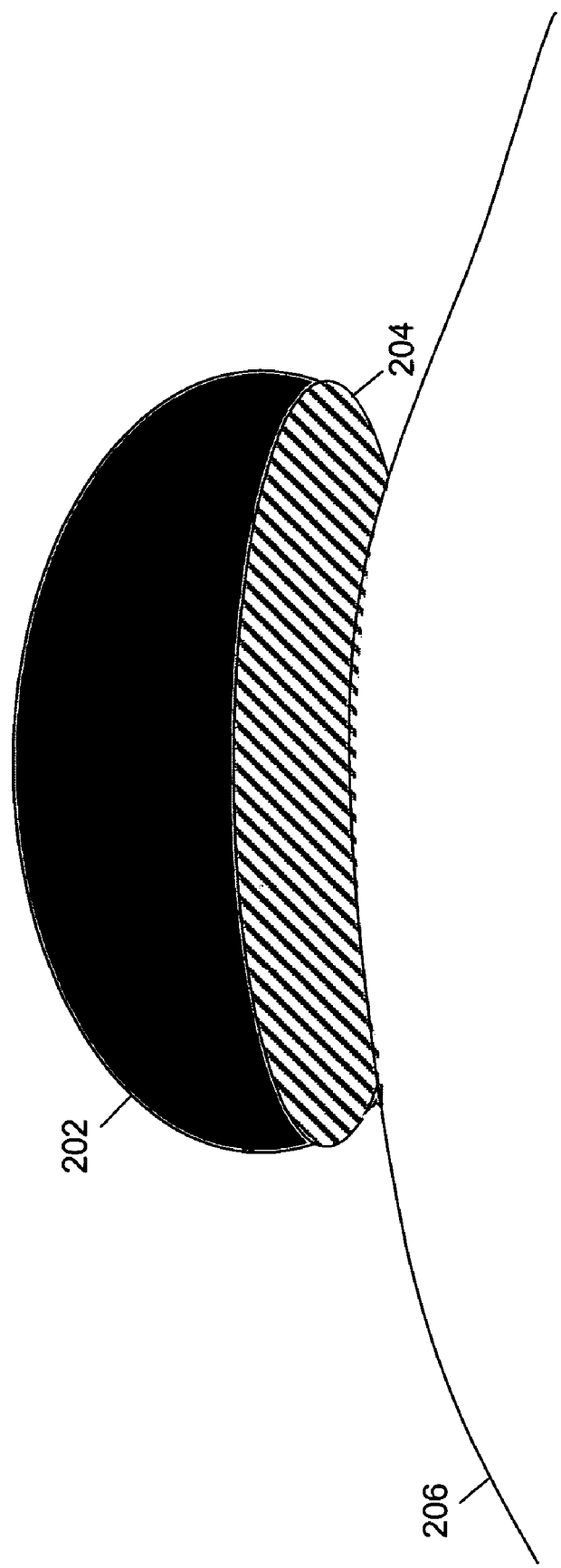
FIG. 2 is a schematic view illustrating various regions of an image.

The steps, as shown in FIG. 1, will now be explained by way of a colonography example. Colonography is a diagnostic method that employs X-rays to image and examine the interiors of a patient's colon. FIG. 2 is a schematic view illustrating various regions of an image. Item of interest 202 is shown with respect to rest of image 206. A transition region 204 is shown between item of interest 202 and rest of image 206. Transition region 204 is indicated by striped shading. It will be apparent to those skilled in the art that the regions of the image (including item of interest 202, transition region 204 and rest of image 206) can be defined in terms of the voxels that represent these regions in the 3D visualization image. Hence, each region of the image corresponds to one class of voxels. At step 102 (as shown in FIG. 1), data representing a scan of human patient's colon is accessed. The data is provided by a computed tomography scanner that scans the patient. The data may be obtained with the patient in supine (lying down, face upwards) or prone (lying down, face downwards) positions. Further, the scan may be performed after dry or wet preparation and with or without tagging of stool. At step 104 (as shown in FIG. 1), a computer aided detection is performed to identify at least one item of interest in the data. Computer aided detection uses at least one characteristic of the data accessed at step 102 delineate the items of interest. Examples of characteristics that can be used to delineate items of interest include shape, size, density, location, and curvature. For example, during colonography, fecal matter present in the colon may be identified as item of interest 202. Examples of methods for identifying and delineating item of interest 202 within the data include iterative thresholding, k-means segmentation, edge detection, edge linking, curve fitting, curve smoothing, morphological filtering, region growing, fuzzy clustering, image or volume measurements, heuristics, knowledge-based rules, decision trees, neural networks and the like. In one embodiment, item of interest 202 is selected by a user. The user may select or delineate item of interest 202 using a suitable interface. For example, the user can select item of interest 202 using a mouse, a touch screen, eye-tracking and/or with the help of voice commands. At step 106, transparency levels of various regions of an image are determined based on sets of rules. The data accessed at step 102 can be used in generating a 3D visualization image. The 3D visualization image is made of a plurality of pixels. Transparency levels of pixels of rest of image 206 in the 3D visualization image are set according to a first set of rules. Transparency levels of pixels representing item of interest 202 are set according to a second set of rules. Further, transparency levels of pixels representing transition area 204 between item of interest 202 and rest of image 206 are set according to a third set of rules. These sets of rules are different from each other. It will be apparent to those skilled in the art that similar sets of rules can be used to set the transparency levels of voxel classes in the 3D visualization image. Finally, at step 108, the 3D visualization image is generated wherein the transparency levels of the pixels is set as determined at step 106.

Figure 3:
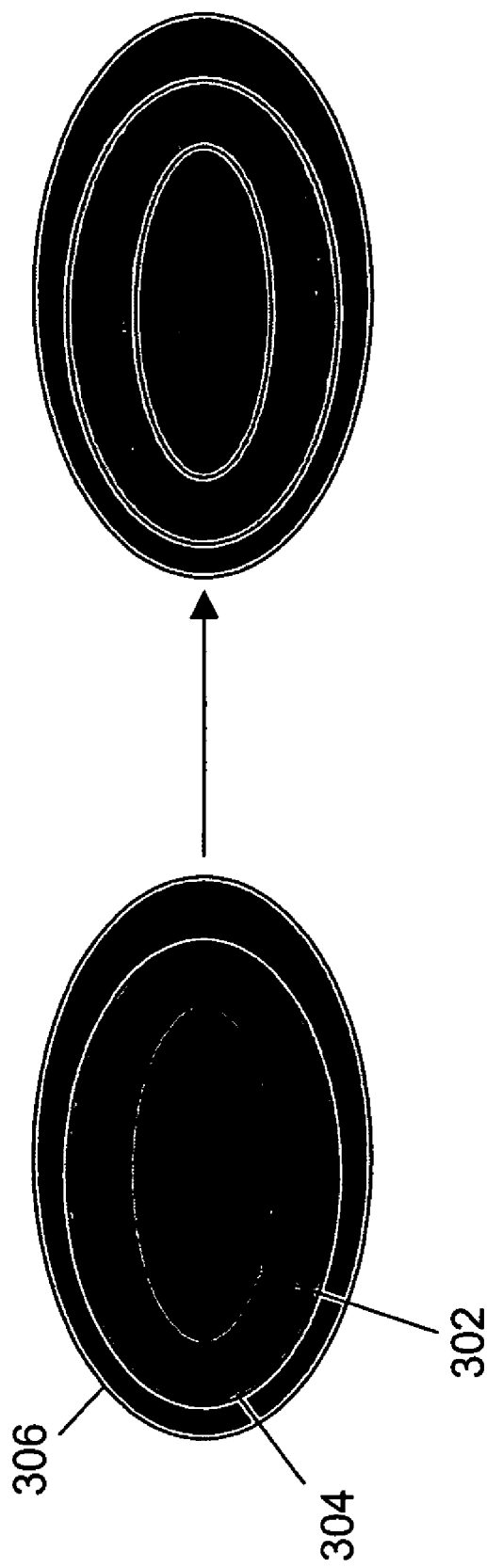
FIG. 3 is an illustration showing a scan of an object that is made transparent with the help of a set of rules.

FIG. 3 is an illustration showing a scan of an object that is made transparent with the help of a set of rules. Area of interest 302, transition area 304 and rest of image 306 are shown in the figure with different shading. The same image after varying the transparency of various pixels is also shown in FIG. 3. After varying the transparency levels, area of interest 302 and transition area 304 are less discernable from rest of image 306.

In most images, pixels are defined using RGB channels. These channels define the intensities of the basic colors (red—R, green—G, and blue—B) for the pixel. Therefore, each pixel is represented as a triplet of RGB channels. Values of the RGB channels for each pixel vary between 0 and 255. A value of 0 means that color is absent from a pixel, and a value of 255 means that the intensity of the color is maximum. For example, (0, 0, 0) is black, whereas (255, 255, 255) is white. Further, (255, 0, 0) is red, (0, 255, 0) is green and (0, 0, 255) is blue.

For the purpose of this invention, to suppress the appearance of item of interest 202 (as shown in FIG. 2), the transparency level of the pixels representing item of interest 202 must be set. The level of transparency is defined by a fourth channel known as the alpha channel. Hence, each pixel is defined using RGBa channels (red—R, green—G, blue—B and alpha—a). Akin to the RGB values, the value of the alpha channel also varies between 0 and 255, with 0 meaning that the pixel is transparent and 255 meaning that the pixel is totally visible. As the image is 3D, if the transparency value of a pixel is set to 0, then the pixel behind it appears. Therefore, once item of interest 202 has been identified at step 104, it is suppressed at step 106 by varying the transparency levels of the pixels representing item of interest 202 according to sets of rules. According to one embodiment, the second set of rules are set so that the transparency levels of at least some pixels representing item of interest 202 are higher than the transparency levels of these pixels if the first set of rules is used to define their transparency levels. This implies that the second set of rules is set so that item of interest 202 is more transparent than rest of image 206. For example, fecal matter identified as an item of interest may be suppressed by setting the transparency levels of the pixels representing the fecal matter to zero. In accordance with another embodiment, the third set of rules is set so that the transparency levels of at least some pixels representing transition area 204 (as shown in FIG. 2) are higher than the transparency levels of these pixels if the first or second set of rules is used to define their transparency levels. This implies that transition area 204 is made the most transparent. In accordance with another embodiment, the third set of rules is set so that transition area 204 is more transparent than item of interest 202, but is more opaque as compared to rest of image 206. For example, the transparency level of a transition region between the fecal matter and the region of the image representing the colon may be set to 127 so that the transition region partially appears in the image. In the case that the fecal matter covers a growth, which is to be detected, then this abnormality may appear in the transition region. However, it may be advantageous to set the transparency of the fecal matter to be 127 so that it does not entirely disappear, yet parts of the 3D image obstructed by the fecal matter, can be seen. This ensures that no abnormal growths within the colon are missed while observing the image. In this case, the level of transparency of the transition region may be set to 191. It will be apparent to those skilled in the art that a variety of such rules may be defined to suppress the various regions of the image.

Figure 4:
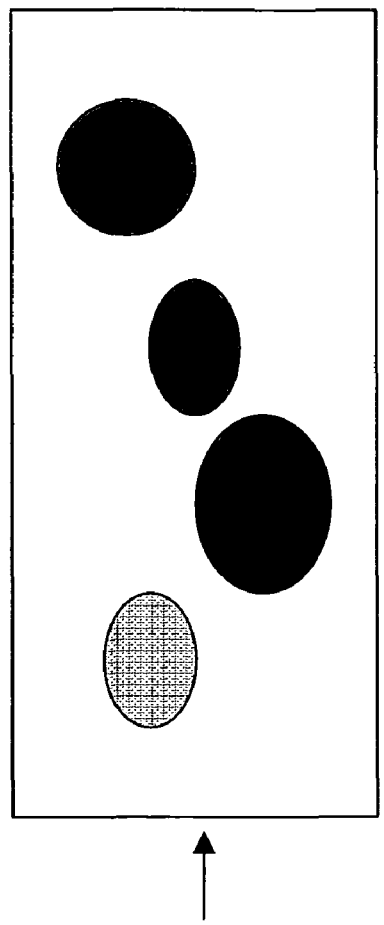
FIG. 4 is an illustration of a scan of an image with a plurality of highlighted items of interest.
Figure 4:
Figure 4:
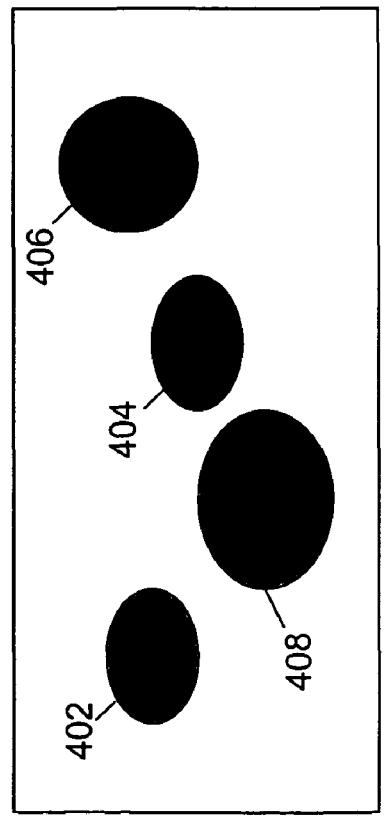

FIG. 4 is an illustration of a scan of an image with a plurality of items of interest highlighted. A set of rules may be defined so that only one item of interest is made partially visible while other items of interest, which have similar intensity values, are not affected. For example, in FIG. 4, an item of interest 402 is selected. The rules are defined so that the transparency levels of the pixels representing item of interest 402 are changed. Other items of interest in FIG. 4 are not made transparent. Such a set of rules must define the pixels that represent the item of interest to be made partially visible and the transparency levels for these pixels.

The sets of rules as mentioned above are a default set of rules. According to another embodiment, these rules are provided by a user before the 3D visualization image is generated. However, a user viewing the generated 3D visualization image may observe that the rules for defining the transparency levels for the image are not appropriate for diagnostic purposes. In accordance with another embodiment of the present invention, the user can then provide transparency levels for the various regions of the image so that a second 3D visualization image with modified transparency levels may be created. These transparency levels are used to change the transparency levels of the pixels of the image so as to adjust the image so that it may be used for diagnostic purposes. For example, the user may observe an abnormal growth in transition area 204. The user can then decrease the transparency level of transition area 204 to study transition area 204 better. Similarly, the user can also change the transparency level for item of interest 202.

Figure 5:
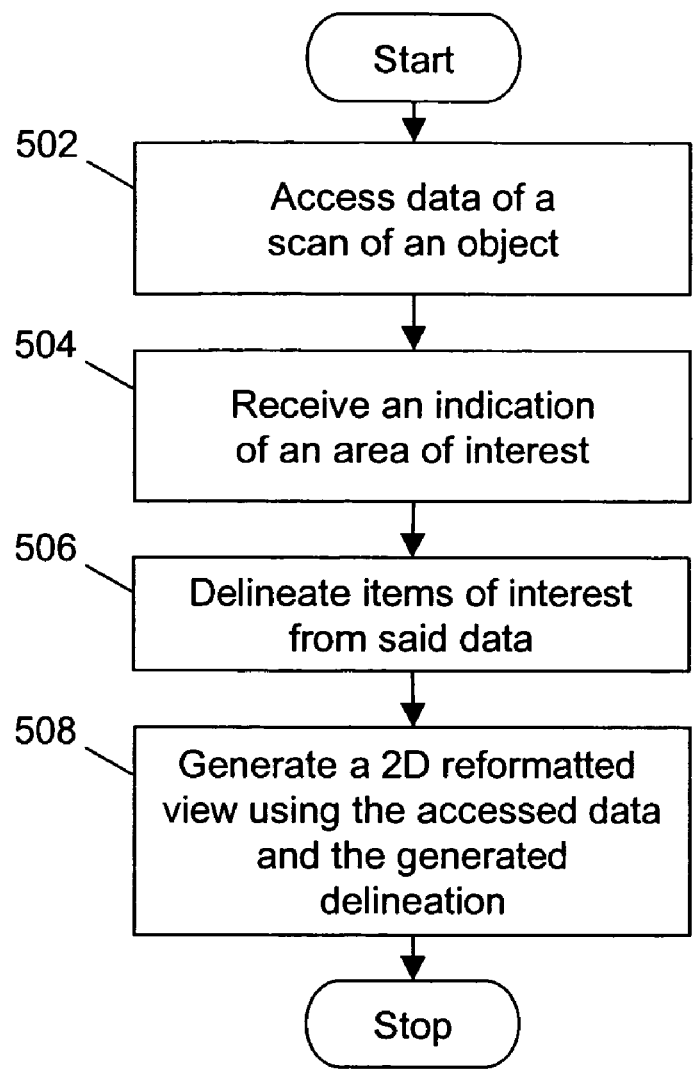
FIG. 5 is a flowchart illustrating the steps for suppressing at least one item of interest during visualization in accordance with an embodiment of the present invention.
Figure 6:
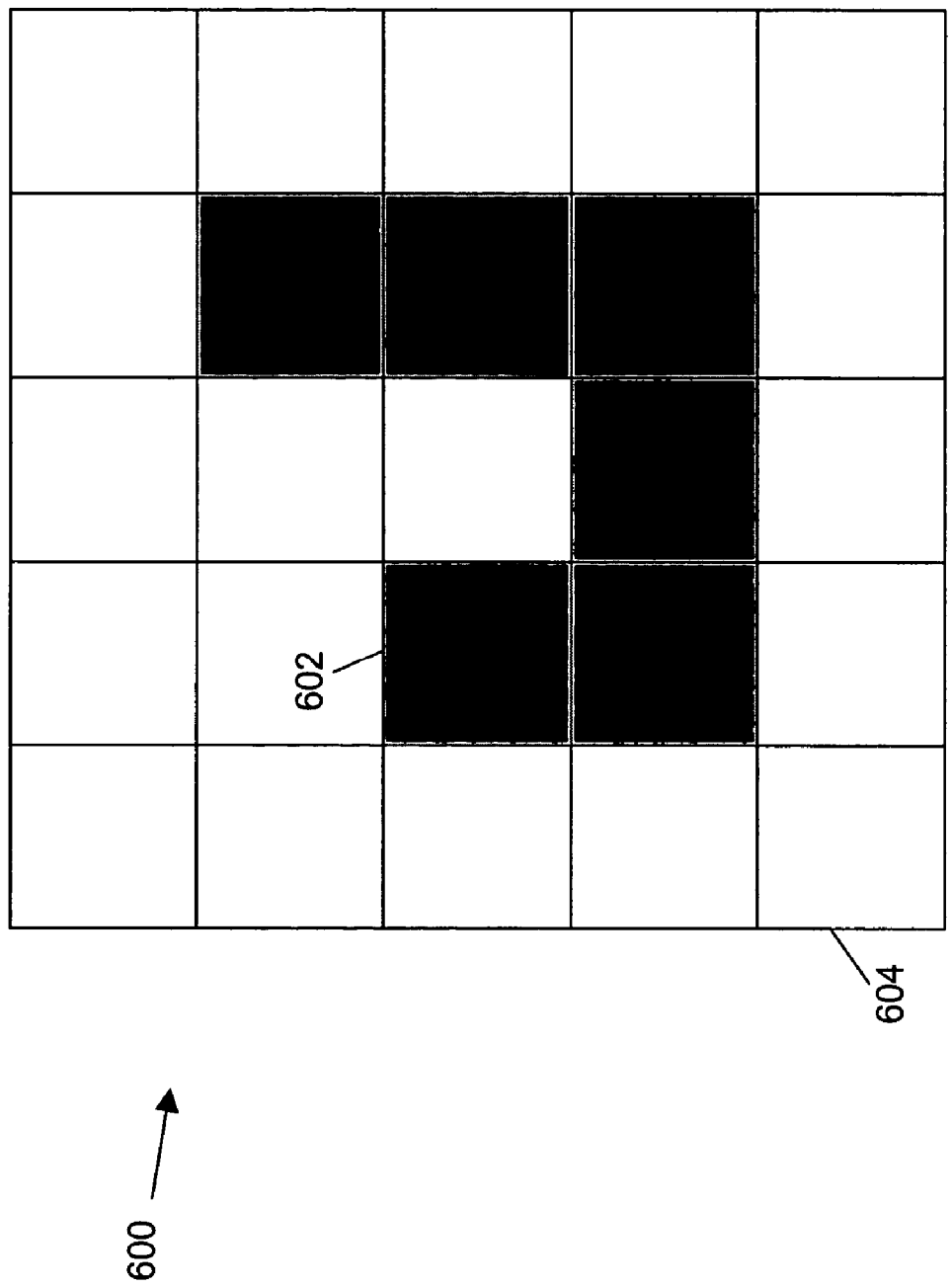
FIG. 6 is a block diagram showing an image from which a segmentation mask is generated.

FIG. 5 is a flowchart illustrating the steps for suppressing at least one item of interest during visualization in accordance with an embodiment of the present invention. At step 502, data for a scan of an object is accessed. This data is accessed, for example, from a computed tomography scanner that scans the object. At step 504, an indication of items of interest is received. This indication may be received, for example, from a user viewing a generated 3D visualization image generated from the received data. The user can delineate the items of interest with the help of a mouse, a touch screen, eye-tracking and/or with the help of voice commands. At step 506, the items of interest are delineated from the accessed data. In accordance with one embodiment of the present invention, a segmentation process is performed on the accessed data to generate a segmentation mask of the items of interest. A segmentation mask is a byte array that contains the same number of elements as the number of pixels of the 3D image. The segmentation mask maps each pixel of the 3D image to a particular region. FIG. 6 is a block diagram showing an image including two regions. An image 600 is made of 25 pixels. Further, image 600 includes two regions, 602 and 604. Region 602 is shaded. A segmentation mask for this image is a 5×5 matrix (i.e., 25 elements), with each element corresponding to one pixel of image 600. The values of the elements denote the region to which a pixel belongs. For example, in the segmentation mask for image 400, the elements corresponding to the pixels in region 602 (shaded gray) will be set to "1". Similarly, the elements corresponding to the rest of image 600, i.e. region 604 (not shaded) will be set to "2". A similar segmentation mask is created for the received data at step 506. The segmentation mask is used to distinguish the items of interest in the received data. Finally, a 2D (two-dimensional) reformatted view of the received data is generated at step 508 (as shown in FIG. 5). This 2D reformatted view is generated using the data accessed at step 502 (as shown in FIG. 5) and the delineation generated at step 506 (as shown in FIG. 5). The intensities of the items of interest in the 2D view are changed according to a set of rules. In one embodiment of the present invention, the intensities of the items of interest are changed so that the items of interest are at least partially removed from the 2D reformatted view. For example, in a visualization of blood vessels, it is required to remove bones. Therefore, in a 3D image of blood vessels, bones can be indicated as items of interest and segmented. A 2D view for the 3D image will have the bones partially or fully removed. In one embodiment of the present invention, the area of interest is at least partially removed by varying the transparency levels of the area of interest. For example, transparency values for all the pixels that form the area of the interest can be reduced to partially remove the area of interest. The pixels that form the area of the interest are identified with the help of the segmentation map. In accordance with another embodiment, the generated 2D view includes an indication of the area of interest, which has been partially removed. This can be done by assigning a particular color to the pixels that represent the border between the area of interest and the rest of the image. A borderline passing through all the pixels that lie between the area of interest and the rest of the image can also be used to indicate the area of interest. For example, in one embodiment and referring to FIG. 2 viewed as a cutaway view, transition area 204 represents a boundary of an item of interest, 202 represents portions interior to the item of interest and 206 represents areas outside the item of interest.

Figure 7:
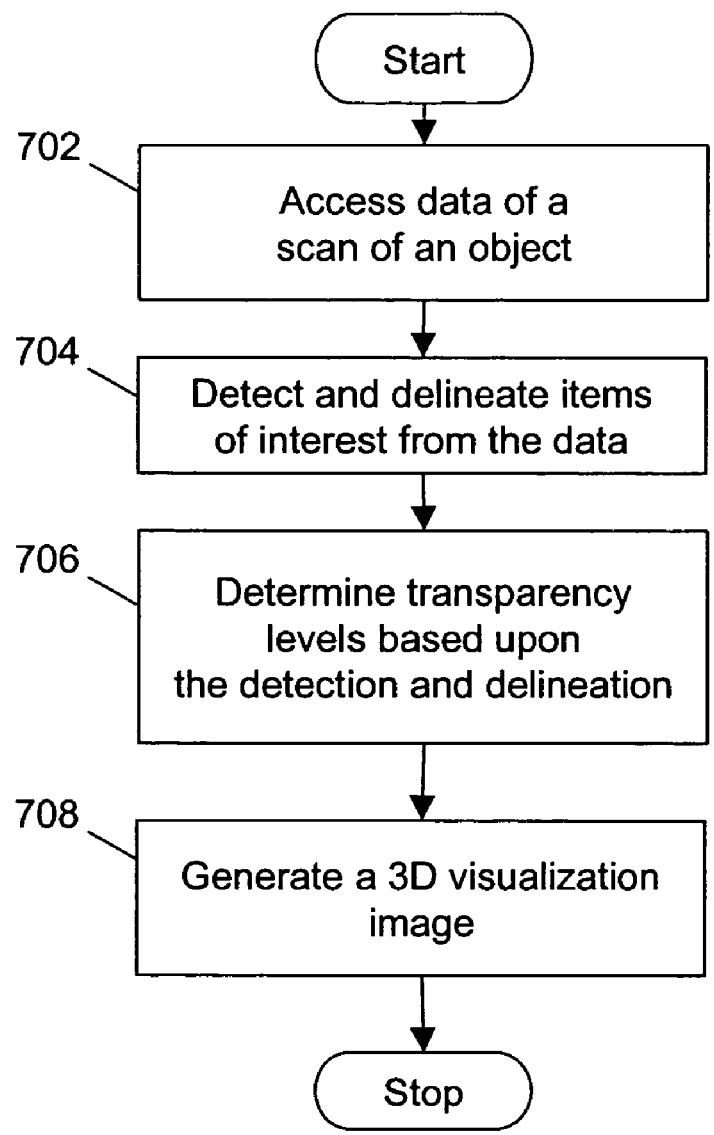
FIG. 7 is a flowchart illustrating the steps for suppressing at least one area of interest during visualization in accordance with an embodiment of the present invention.

FIG. 7 is a flowchart illustrating the steps for suppressing at least one item of interest during visualization in accordance with an embodiment of the present invention. At step 702, data of a scan of an object is accessed. At step 704, items of interest are detected and delineated from the accessed data. In accordance with one embodiment of the present invention, items of interest are detected and delineated with the help of Computer Aided Detection (CAD). Items of interest can be defined in several ways using the entire data as accessed at step 702 or using a part of the data. Examples of methods for identifying the item of interest within the accessed data include iterative thresholding, k-means segmentation, edge detection, edge linking, curve fitting, curve smoothing, morphological filtering, region growing, fuzzy clustering, image or volume measurements, heuristics, knowledge-based rules, decision trees, neural networks and the like. In automatic computer detection and delineation, an automatic segmentation algorithm uses feature extraction and prior knowledge to automatically delineate the items of interest. Multiple features can be extracted from the image data using item of interest statistics such as shape, size, texture, intensity, gradient, edge strength, location, proximity, histogram, symmetry, eccentricity, orientation, boundaries, moments, fractal dimensions, entropy, density, curvature and the like. Other information that can be used for feature extraction includes acquisition-based information (e.g., kVp, dose) and patient-based information (e.g., age, gender, smoking history). Prior knowledge is obtained from training. The training phase involves the computation of several candidate features on known samples of normal and abnormal items of interest. A feature selection algorithm is employed to sort through features and select only the useful ones and remove those that provide no information or redundant information. Optimal feature selection can be performed using a well-known distance measure including divergence measure, Bhattacharya distance, Mahalanobis distance and the like. A combination of automatic detection and manual delineation can also be used to detect and delineate items of interest. At step 706, transparency levels for various regions of an image are obtained on the basis of the detection and delineation carried out at step 704. At step 708, a 3D visualization image is generated from the accessed data wherein transparency values of the pixels of the 3D visualization image are varied based upon the delineated items of interest and a set of rules. In accordance with one embodiment of the present invention, the transparency values of the pixels of the 3D visualization image are set so that the interior of the items of interest is substantially transparent. For example, to make the interior of the items of interest substantially transparent, the levels of transparency for the pixels representing the delineated items of interest can be set to 192. In accordance with another embodiment of the present invention, transition areas are also delineated at step 504. To identify the items of interest, the set of rules can be defined such that the levels of transparency for the items of interest are set to 255 and the levels of transparency for the transition areas are set to 192. Hence, the items of interest are completely transparent in the 3D visualization view. However, the transition areas are partially visible and the items of interest can be identified.

Figure 8:
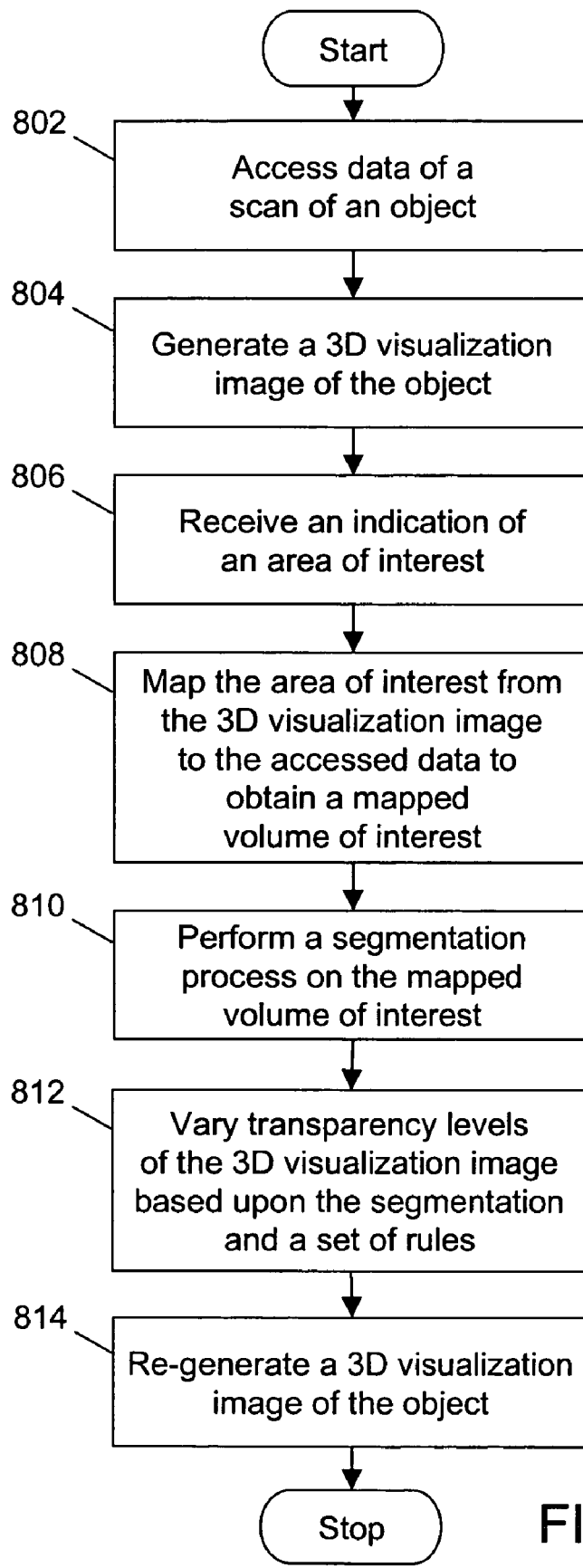
FIG. 8 is a flowchart illustrating the steps for suppressing at least one area of interest during visualization in accordance with an embodiment of the present invention.

FIG. 8 is a flowchart illustrating the steps for suppressing at least one area of interest during visualization in accordance with an embodiment of the present invention. At step 802, data of a scan of an object is accessed. This data is used in generating a 3D visualization image at step 804. At step 806, an indication of an area of interest is received. This indication may be received, for example, from a user viewing the generated 3D visualization image generated from the received data. The user can delineate the area of interest with the help of a mouse, a touch screen, eye-tracking and/or with the help of voice commands. At step 808, the area of interest is mapped from the 3D visualization image to the accessed data. This is done to obtain a mapped volume of interest. For example, a mapping that maps the pixels in the 3D visualization image that represent the area of interest to the data corresponding to these pixels in the accessed data can be generated. At step 810, a segmentation process is performed on the mapped volume of interest. In accordance with one embodiment of the present invention, the segmentation process is performed to generate a segmentation mask for the 3D visualization image based on the mapped volume of interest. The segmentation mask can be used to vary the transparency values of the 3D visualization image at step 812 (as described above in conjunction with FIG. 4). The transparency levels can be varied according to a set of rules that define the transparency levels of the segments of the 3D visualization image so that the area of interest is made to appear partially or substantially transparent. Finally, at step 814, the 3D visualization image is re-generated wherein the transparency levels of the pixels are set based on the set of rules.

The methods for suppressing items and areas of interest during visualization and the steps involved therein, as described in the present invention or any of its components, may be embodied in the form of a computer program that is executed on a computer system. Typical examples of a computer system includes a general-purpose computer, a programmed microprocessor, a micro-controller, a peripheral integrated circuit element, and other devices or arrangements of devices that are capable of implementing the steps that constitute the method of the present invention.

The computer system comprises a computer, an input device, a display unit, and the Internet. The computer further comprises a microprocessor. The microprocessor is connected to a communication bus. The computer also includes a memory. The memory may include Random Access Memory (RAM) and Read Only Memory (ROM). The computer system further includes a storage device. The storage device can be a hard disk drive or a removable storage drive such as a floppy disk drive, optical disk drive, etc. The storage device can also be other similar means for loading computer programs or other instructions into the computer system. The computer system also includes a communication unit. The communication unit allows the computer to connect to other databases and the Internet through an I/O interface. The communication unit allows the transfer as well as reception of data from other databases. The communication unit may include a modem, an Ethernet card, or any similar device, which enables the computer system to connect to databases and networks such as LAN, MAN, WAN, and the Internet. The computer system facilitates inputs from a user through input device, accessible to the system through I/O interface.

The computer system executes a set of instructions that are stored in one or more storage elements, in order to process input data. The storage elements may also hold data or other information as desired. The storage element may be in the form of an information source or a physical memory element present in the processing machine.

The set of instructions may include various commands that instruct the processing machine to perform specific tasks such as the steps that constitute the method of the present invention. The set of instructions may be in the form of a software program. Further, the software may be in the form of a collection of separate programs, a program module with a larger program or a portion of a program module, as in the present invention. The software may also include modular programming in the form of object-oriented programming. The processing of input data by the processing machine may be in response to user commands, results of previous processing, or a request made by another processing machine. Further, the computer system executes an operating system. Exemplary operating systems with which the invention may be implemented include Microsoft Windows™, Unix, and Linux.

Technical effects of the herein described methods include the potential for improving the use of 3D computed tomography images in medical diagnostics. In many cases, the presence of irrelevant bodies in images generated blocks the view of areas that are to be studied in the image. For example, computed tomography is used in detecting abnormal growths in the colon. However, the presence of fecal matter in the colon obstructs the visualization of the colon. Similarly, the presence of bones obstructs the visualization of blood vessels. The present invention allows these obstructions to be partially or totally removed from the 3D images. The methods described above can be used with volume rendering methods including a fly-through 3D visualization of a segmented colon and rendering a virtually dissected colon to increase the sensitivity of CT colonography.

As used herein, an element or step recited in the singular and proceeded with the word "a" or "an" should be understood as not excluding plural said elements or steps, unless such exclusion is explicitly recited. Furthermore, references to "one embodiment" or "an embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

While the invention has been described in terms of various specific embodiments, those skilled in the art will recognize that the invention can be practiced with modification within the spirit and scope of the claims.

What is claimed is:

1. A method for generating an image using an imaging system, said method comprising:
    accessing data of a scan of an object;
    delineating, via a processor, at least one item of interest in the accessed data using at least one physical characteristic, the at least one physical characteristic comprising at least one of a shape, a size, a density, a location, and a curvature of the at least one item of interest;
    setting a transparency value for a first set of pixels that do not represent the at least one item of interest according to a first set of rules;
    setting a transparency value for a second set of pixels that represent an interior portion of the at least one item of interest according to a second set of rules, the second set of rules being different than the first set of rules;
    setting a transparency value for a third set of pixels that represent a transition area between the first set of pixels and the second set of pixels according to a third set of rules, the third set of rules being different from the first set of rules and the second set of rules;
    generating an image of the object using the accessed scan data and the first, second, and third sets of rules, the image comprising a three-dimensional (3D) visualization image having transparency levels for the first set of pixels set according to the first set of rules, transparency levels for the second set of pixels set according to the second set of rules, and transparency levels for the third set of pixels set according to the third set of rules; and adjusting a transparency value for pixels representing the delineated at least one item of interest, wherein said adjusting the transparency value does not affect the transparency value for pixels in any other pixels of the image.

2. A method in accordance with claim 1 wherein generating the image comprises generating a 3D visualization image wherein transparency levels for the first set of pixels are set according to the first set of rules, transparency levels for the second set of pixels are set according to the second set of rules such that a pixel in the second set of pixels has a higher transparency level with the second set of rules than with the first set of rules.

3. A method in accordance with claim 1 wherein generating the image comprises generating a 3D visualization image wherein transparency levels for the first set of pixels are set according to the first set of rules, transparency levels for the second set of pixels are set according to the second set of rules such that a pixel in the second set of pixels has a higher transparency level with the second set of rules than with the first set of rules, and transparency levels for the third set of pixels is set according to the third set of rules such that a pixel in the transition area has a transparency level less with the third set of rules than with the first and second sets of rules.

4. A method in accordance with claim 1 wherein generating the image comprises generating a 3D visualization image wherein transparency levels for the first set of pixels are set according to the first set of rules, transparency levels for the second set of pixels are set according to the second set of rules such that a pixel in the second set of pixels has a higher transparency level with the second set of rules than with the first set of rules, and transparency levels for the third set of pixels are set according to the third set of rules such that at least one pixel in the third set of pixels has a transparency level less with the third set of rules than with the second set of rules and greater with the third set of rules than with the first set of rules.

5. A method in accordance with claim 1 wherein delineating at least one item of interest in the data comprises delineating the at least one item of interest wherein a user has selected the at least one item of interest.

6. A method in accordance with claim 1 wherein delineating the at least one item of interest in the data comprises delineating the at least one item of interest comprising fecal matter.

7. A method in accordance with claim 1 wherein at least one of the first, second, and third set of rules is received from a user.

8. A method in accordance with claim 1 further comprising:
receiving an transparency level from a user; and
generating a second 3D visualization image wherein transparency levels for at least some pixels representing the interior portion of the item of interest are set according to the received transparency level.

9. A method in accordance with claim 1 further comprising:
receiving an transparency level from a user; and
generating a second 3D visualization image wherein transparency levels for at least some pixels representing the transition area are set according to the received transparency level.

10. A method in accordance with claim 1 further comprising:
receiving a first transparency level from a user;
receiving a second transparency level from a user;
generating a second 3D visualization image wherein transparency levels for at least some pixels representing the interior portion of the item of interest are set according to the received first transparency level and at least some pixels representing the transition area are set according to the received second transparency level.

11. A method in accordance with claim 1, wherein the imaging system comprises a computed tomography scanner, accessing data of a scan of an object comprises accessing X-ray data acquired by the computed tomography scanner during the scan of the object.

12. A method for generating an image using an imaging system, said method comprising:
accessing data of a scan of an object;
delineating, via a processor items of interest from the accessed data, the delineated items of interest including at least one similar physical characteristic represented by the accessed data, the at least one similar physical characteristic comprising at least one of a shape, a size, a density, a location, and a curvature of the items of interest;
defining a set of rules for setting an intensity for at least one item of interest of the delineated items of interest; and
generating an image using the accessed data and the delineated items of interest such that the intensity of the at least one item of interest is displayed in the image according to the defined set of rules, wherein adjusting the set of rules applied to the at least one item of interest does not affect the intensity of any other delineated items of interest, and the image comprising a two-dimensional (2D) reformatted view.

13. A method in accordance with claim 12 further comprising generating a 2D reformatted view using the accessed data and the delineated items of interest such that the at least one item of interest is at least partially removed from the 2D reformatted view.

14. A method in accordance with claim 12 wherein generating the image further comprises changing transparency values for pixels within the at least one item of interest.

15. A method in accordance with claim 14 further comprising receiving from a user a selection of the at least one item of interest comprising bone.

16. A method for generating an image using an imaging system, said method comprising:
accessing data of a scan of an object;
detecting and delineating items of interest from the data via a processor, the items of interest including at least one similar physical characteristic represented by the accessed data, the at least one similar physical characteristic comprising at least one of a shape, a size, a density, a location, and a curvature of the items of interest;
defining a set of rules for setting a transparency value for at least one item of interest of the delineated items of interest; and
generating an image using the accessed data, the second image comprising a three-dimensional (3D) visualization image having at least the transparency value for the at least one item of interest varied based upon the delineated items of interest and the defined set of rules, wherein adjusting the set of rules for setting the transparency value for the at least one item of interest does not affect the transparency of any other delineated items of interest.

17. A method in accordance with claim 16 wherein
detecting and delineating items of interest from said data further comprises detecting and delineating items of interest from said data such that at least two items of interest of the delineated items of interest include substantially equal intensity values;
defining a set of rules further comprises defining a set of rules for setting a transparency value for a first item of interest of the at least two items of interest; and
generating an image further comprises generating a 3D visualization image wherein at least the transparency value for the first item of interest is varied and a transparency value of a second item of interest of the at least two items of interest is held constant based upon the delineated items of interest and the defined set of rules.

18. A method for generating an image using an imaging system, said method comprising:
accessing data of a scan of an object;
generating a first three-dimensional (3D) visualization image of the object using the accessed data;
displaying the generated first 3D visualization image on a display;
receiving, via a user interface, an indication of an area of interest, the area of interest selected from the first 3D visualization image as displayed, the area of interest selected based on at least one of a shape, a size, a density, a location, and a curvature of the area of interest as visualized;
defining a set of rules for setting a transparency value for the area of interest;
mapping the area of interest from the first 3D visualization image to the data to obtain a mapped volume of interest;
performing a segmentation process on the mapped volume of interest, via a processor, to delineate at least one item of interest;
varying transparency values of the first 3D visualization image based upon the segmentation and the defined set of rules, wherein varying the transparency value of the delineated item of interest does not vary the transparency value of any other areas in the 3D visualization image; and
generating a second 3D visualization image using the accessed data, the second 3D visualization image having the varied transparency levels.

19. A method in accordance with claim 18 wherein varying transparency values based upon the segmentation comprises varying transparency values based upon the segmentation such that the interior of the area of interest is substantially transparent.

20. A method in accordance with claim 18 wherein varying transparency values based upon the segmentation comprises varying transparency values based upon the segmentation such that the interior of the area of interest is substantially transparent and a transition area is delineated to enable a viewer of the 3D visualization image to identify the area of interest.

21. A non-transitory computer readable medium encoded with a program configured to instruct a computer to:
access scan data;
delineate the accessed scan data into at least three classes of voxels, voxels within each class of voxels including a similar physical characteristic represented by the accessed scan data, the similar physical characteristic comprising at least one of a shape, a size, a density, a location, and a curvature of each class of voxels;
define a first set of rules for setting a transparency value for a first class of voxels;
define a second set of rules for setting a transparency value for a second class of voxels;
define a third set of rules for setting a transparency value for a third class of voxels;
apply a transparency level to each class of voxels based on the sets of rules;
render the data to form an image using the accessed scan data, the image comprising a three-dimensional (3D) image; and
vary the transparency value for the first class of voxels, wherein said varying the transparency value does not affect the transparency of any other voxels in the image.

22. A non-transitory computer readable medium encoded with a program configured to instruct a computer to:
access scan data;
delineate the accessed scan data into regions using a processor;
group the delineated regions into at least three classes of regions, via the processor, each class of regions includes a similar physical characteristic represented by the accessed scan data, the at least one similar physical characteristic comprising at least one of a shape, a size, a density, a location, and a curvature of each class of regions;
define a set of rules for setting an intensity for at least one class of regions;
change the intensity in at least one delineated region according to the defined set of rules, wherein changing the intensity in at the least one delineated region does not change the intensity in any other area of the scan data; and
generate an image using the accessed scan data and the changed intensity.

23. A medium in accordance with claim 22, wherein said program is further configured to instruct the computer to render the data to generate a three-dimensional (3D) image as the image.

24. A medium in accordance with claim 22, wherein said program is further configured to instruct the computer to reformat the data to generate a two-dimensional (2D) image as the image.

25. A non-transitory computer readable medium encoded with a program configured to instruct a computer to:
access scan data;
perform a computer aided detection, via a processor, on the first image to identify at least one item of interest using a physical characteristic represented by the scan data, the physical characteristic comprising at least one of a shape, a size, a density, a location, and a curvature of the at least one item of interest;
define a set of rules for setting a transparency level for at least one item of interest;
vary transparency levels of the scan data based on the at least one item of interest and the defined set of rules, wherein varying the level of the scan data for the at least one item of interest does not affect the scan data in any other area of the scan; and
render the scan data to form an image using the accessed scan data, the image comprising a three-dimensional (3D) image.

26. A non-transitory computer readable medium encoded with a program configured to instruct a computer to:
access scan data;

render the accessed scan data to form a first image that is a three-dimensional (3D) image;

receive from a user via a user interface an indication of at least one region of interest within the first image as displayed to the user, the at least one region of interest indicated based on at least one of a shape, a size, a density, a location, and a curvature of the at least one region of interest as rendered;

map the at least one region of interest onto the accessed scan data to generate a volume of interest;

segment the volume of interest to generate a segmentation mask for the first image, the segmentation mask including a first set of pixels corresponding to the at least one region of interest and a second set of pixels corresponding a remainder of the volume of interest that is not the at least one region of interest;

define a set of rules that define a transparency level for at least the first set of pixels;

vary transparency levels of the first image based on the segmentation mask and the set of rules, wherein varying the transparency level for the at least first set of pixels does not vary the transparency level of any other pixels of the first image; and render the accessed scan data to generate a second image having the varied transparency levels.

* * * * *